US00PP10427P

United States Patent [19]

Danziger

[11] Patent Number: Plant 10,427

[45] Date of Patent: Jun. 2, 1998

[54] PETUNIA PLANT NAMED 'CASCHIKA'

[75] Inventor: Gabriel Danziger, Nir Tzvi, Israel

[73] Assignee: Danziger - "Dan" Flower Farm, Moshav Mishmar Hashiva, Israel

[21] Appl. No.: 660,172

[22] Filed: Jun. 3, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 8,889 | 9/1994 | Danziger | Plt./68.1 |
| P.P. 8,914 | 9/1994 | Danziger | Plt./68.1 |
| P.P. 8,915 | 9/1994 | Danziger | Plt./68.1 |
| P.P. 8,934 | 10/1994 | Danziger | Plt./68.1 |
| P.P. 9,322 | 10/1995 | Tachibana et al. | Plt./68.1 |
| P.P. 9,341 | 10/1995 | Tachibana et al. | Plt./68.1 |
| P.P. 9,342 | 10/1995 | Sakazaki et al. | Plt./68.1 |
| P.P. 9,408 | 12/1995 | Rother | Plt./68.1 |
| P.P. 9,556 | 5/1996 | Tachibana et al. | Plt./68.1 |
| P.P. 9,577 | 6/1996 | Suzuki et al. | Plt./68.1 |

*Primary Examiner*—James R. Feyrer
*Assistant Examiner*—Kent L. Bell

[57] ABSTRACT

The petunia cultivar 'Caschika' is particularly characterized by vigorous growth and continued flowering under hot summer conditions and in mild winters; a long garden season with flowering from early spring until late winter; prolific growth with vigorous green-gray (R.H.S. 137B) foliage and pink-lavender (R.H.S. 78A) flowers.

1 Drawing Sheet

The present invention comprises a new and distinct cultivar of petunia known by the cultivar name 'Caschika'.

'Caschika' was originated from a hybridization made by the inventor in a controlled breeding program in Mishmar Hashiva, Israel in 1995. The female parent was a proprietary line designated CV 42 and the male parent was a proprietary line designated CV 13. 'Caschika' was discovered and selected as one flowering plant within the progeny of the stated cross by the inventor Gaby Danziger in May 1995 in a controlled environment in Mishmar Hashiva.

The first act of asexual reproduction of 'Caschika' was accomplished when vegetative cuttings were taken from the initial selection in June 1995 in a controlled environment in Mishmar Hashiva by the inventor. Horticultural examination of selected units initiated in September 1995 has demonstrated that the combination of characteristics as herein disclosed for 'Caschika' are firmly fixed and are retained through successive generations of asexual reproduction.

'Caschika' has not been observed under all possible environmental conditions. The phenotype may vary somewhat with variations in environment such as temperature, light intensity and day length, without any variation in genotype. The following observations, measurements and comparisons describe the plants grown in Mishmar Hashiva under greenhouse conditions which approximate those generally used in commercial practice.

The following traits have been repeatedly observed and are determined to be basic characteristics of 'Caschika' which in combination distinguish this petunia as a new and distinct cultivar:

1. Excellent garden performance under full sunlight and also suitable for indoor usage.

2. Good weather tolerance including vigorous growth and flowering under hot weather conditions and continued flowering through moderate winters.

3. Prolific growth with vigorous green-gray foliage. p 4. Numerous pink-lavender (R.H.S. 78A) flowers of medium size. The cultivar flowers early in the growing season.

5. Long garden season maintaining growth and flowering from early spring until late winter.

6. The cultivar is not particularly susceptible to common petunia diseases.

Of the many commercial cultivars known to the inventor, the most similar in comparison to 'Caschika' is 'Charisma'. In comparison to 'Charisma', however, 'Caschika' has better garden performance due to its vigorous growth and distinctive flower color. Unlike 'Charisma', the cultivar 'Caschika' continues to flower during moderate winter conditions.

The accompanying photographic drawing shows typical flower and foliage characteristics of 'Caschika', with the color being as true as possible with illustrations of this type.

Sheet 1 is a side view of a typical specimen of the variety 'Caschika' showing the abundant flowering, distinctive flower color and plant shape.

In the following description, color references are made to The Royal Horticultural Society Colour Chart. The color values were determined between 10:00–12:00 a.m. on January, 1996 under full sunlight at Mishmar, Hashiva.

Classification:
- *Botanical.*—Petunia hybrid.
- *Commercial.*—Petunia cultivar.

'Caschika' plant:
- *Growth habit.*—Prolific and fast growing.
- *Plant height.*—8–10 inches.
- *Spreading area.*—30 inches.
- *Blooming period.*—Throughout year.

Stem:
- *Thickness.*—2–3 mm.
- *Color.*—Green (R.H.S. 137B).
- *Pubescence.*—Yes.
- *Branching.*—Free.
- *Length of internode.*—10–20 mm.

Leaf:
- *Arrangement on stem.*—Alternate.
- *Shape.*—Ovate.
- *Size.*—Length: 75 mm. Width: 50 mm.
- *Thickness.*—0.2 mm.
- *Color.*—Green-Gray (R.H.S. 137B).
- *Pubescence.*—Yes.

Flower:

*Orientation at opening.*—Upright.

*Type.*—Single.

*Shape.*—Regular and rounded with a united corolla that has 5 lobes and a long straight tube.

*Diameter.*—40–50 mm.

*Color.*—Upper surface: Pink-lavender (R.H.S. 78A), dark eye (R.H.S. 83B). Lower surface: Pink-lavender (R.H.S. 78A).

*Peduncle.*—Length: 15–20 mm. Color: Green (R.H.S. 137B).

*Reproductive organs.*—Pistil: Number: 1. Color: Green (R.H.S. 138C). Stamens: Number: 5. Anther: Gray-Blue (R.H.S. 96C). Filament: Green (R.H.S. 138D).

Disease resistance: The 'Caschika' is not particularly susceptible to common diseases of petunia.

I claim:

1. A new cultivar of petunia plant named 'Caschika' as herein shown and described.

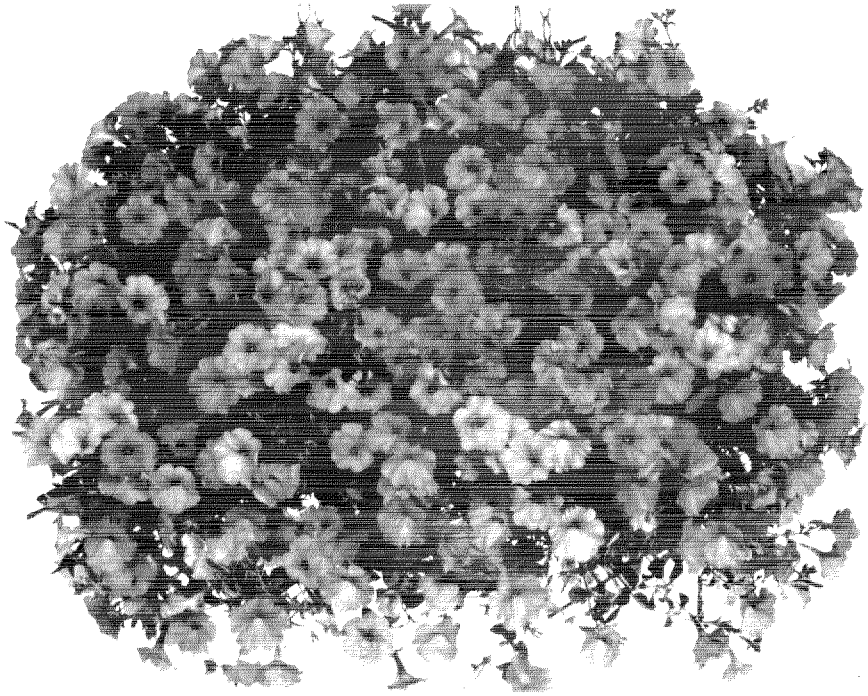

* * * * *